United States Patent
Dupuis et al.

[11] Patent Number: 6,031,043
[45] Date of Patent: Feb. 29, 2000

[54] TOPICAL COMPOSITION COMPRISING A HYDROPHILIC GELLING AGENT OF POLYESTER SULPHONE TYPE

[75] Inventors: Christine Dupuis, Paris; Henri Samain, Bievres, both of France

[73] Assignee: L'Oreal, France

[21] Appl. No.: 09/039,400

[22] Filed: Mar. 16, 1998

[30] Foreign Application Priority Data

Mar. 14, 1997 [FR] France ................................ 97 03117

[51] Int. Cl.$^7$ .......................... C08L 67/02; C08G 63/688; A61K 7/02
[52] U.S. Cl. .......................... 524/603; 523/102; 523/105; 424/60; 424/401; 528/295
[58] Field of Search .................... 523/102, 105; 528/295; 424/60, 401; 524/603

[56] References Cited

U.S. PATENT DOCUMENTS

| | | | |
|---|---|---|---|
| 4,300,580 | 11/1981 | O'Neill et al. | 132/7 |
| 4,525,524 | 6/1985 | Tung et al. | 524/601 |
| 5,744,129 | 4/1998 | Dobbs et al. | 424/61 |

FOREIGN PATENT DOCUMENTS

WO 96/03964  2/1996  WIPO .

OTHER PUBLICATIONS

Minako Juchi et al., "Cosmetics Containing Polyester Particles", Chemical Abstracts, vol. 120, No. 14, Apr. 4, 1994, JP 05310530.

*Primary Examiner*—Tae Yoon
*Attorney, Agent, or Firm*—Finnegan, Henderson, Farabow, Garrett & Dunner

[57] ABSTRACT

A topical composition comprising an aqueous phase containing a hydrophilic gelling agent of polyester sulphone type selected from water-soluble or water-dispersible terephthalic copolyester oligomers comprising repeating dicarboxylate units of formula (I):

$$CO—A—CO—O(CH_2CH_2O)_n$$

wherein the weight-average molecular mass of the copolyester oligomer is less than 20,000, preferably less than 15,000, and a cosmetic treatment process for the skin, mucous membranes or the exoskeleton, in which a composition according to the invention is applied to the skin, mucous membranes or the exoskeleton.

23 Claims, No Drawings

TOPICAL COMPOSITION COMPRISING A HYDROPHILIC GELLING AGENT OF POLYESTER SULPHONE TYPE

Applicants reference herein the patent application of CHRISTINE DUPUIS, HENRI SAMAIN, VÉRONIQUE ROULIER, and VÉRONIQUE FERRARI for TOPICAL AQUEOUS COMPOSITION, Application Ser. No. 09/039,399 filed on even date herewith and incorporate the disclosure thereof specifically by reference herein.

The present invention relates to a novel topical composition comprising a specific gelling material.

Various common gelling agents or thickeners are known for the preparation of topical compositions, in particular algal extracts such as agar—agar, carrageenans, alginates; gums extracted from seeds, plant exudates or microorganism exudates, cellulose derivatives; fruit extracts such as pectins; gelling agents of animal origin such as gelatin, caseinates or water-soluble gelling synthetic polymers such as crosslinked polyacrylic acids. Such gelling agents make it possible to adapt the viscosity of topical compositions depending on their mode of application and the desired effect. However, they have certain drawbacks; in particular, when their concentration in the compositions is increased, they rapidly give very viscous products that are difficult to shape, which also reduces the spreading properties of these compositions and their ease of use on the skin, mucous membranes or the exoskeleton, and reducing in particular their cosmetic application properties.

The inventors have now observed that by using a specific gelling material, it is possible to obtain topical compositions in various liquid, pasty or solid forms while at the same time retaining good ease of topical application.

The inventors have also found that by using this specific gelling agent, it is possible to obtain a film after application and drying of a gelled composition comprising it, the film and its constituents not transferring onto supports with which they may come into contact (for example fabrics, glasses, cups, etc.).

A subject of the present invention is thus a topical composition comprising an aqueous phase which comprises a specific hydrophilic gelling agent of polyester sulphone type.

The specific gelling agents that are useful according to the invention are water-soluble or water-dispersible terephthalic copolyester oligomers essentially comprising repeating dicarboxylate units of formula (I):

$$—CO—A—CO—O—(CH_2CH_2O)_n- \qquad (I)$$

in which
A represents a 1,4-phenylene, sulpho-1,3-phenylene or 1,3-phenylene group,
n ranges from 1 to 4,
at least 35 mol % of the units of formula (I) being units of formula (I) for which A represents a 1,4-phenylene group and n is equal to 1,
at least 7 mol % of the units of formula (I) being units of formula (I) for which A represents a sulpho-1,3-phenylene group,
the weight-average molecular mass of the copolyester oligomers being less than 20,000, preferably less than 15,000.

More preferably, at least 40 mol %, and even more preferably from 40 to 90 mol %, of the units of formula (I) are units of formula (I) for which A represents a 1,4-phenylene group and n is equal to 1.

More preferably, at least 10 mol %, and even more preferably from 10 mol % to 25 mol %, of the units of formula (I) are units of formula (I) for which A represents a sulpho-1,3-phenylene group.

The ends of the chains of the copolyester oligomers can be similar or different and can be represented by groups of formula (I'):

$$—CO—A—CO—O—(CH_2CH_2O)_n—OH \qquad (I')$$

in which A and n are defined above.

The oligomers can also have at the chain ends, and in smaller amounts, groups of formulae

-A—CO—OH

-A—CO—OR in which formulae A is defined above and R represents a $C_1$–$C_4$ alkyl group.

When A represents a sulpho-1,3-phenylene group, it is more particularly an alkali metal sulphonate, in particular sodium or potassium sulphonate, or an ammonium or lower mono-, di-, tri- or tetraalkylammonium sulphonate. According to the invention, the term lower alkylammonium is preferably understood to refer to an ammonium in which the alkyl radical(s) is(are) lower alkyls, preferably $C_1$–$C_6$ alkyls. Preferably, it is a sodium sulphonate.

The copolyester oligomer can optionally comprise up to 20 mol %, more preferably up to 5 mol %, of units of formula (I) for which A represents a 1,3-phenylene group.

According to a preferred embodiment of the invention, the above copolyester oligomer has a weight-average molecular mass ranging from 5000 to 14,000, more preferably from 8000 to 10,000.

The weight-average molecular masses are measured by gel permeation chromatography in dimethylacetamide containing $10^{-2}$ N of LiBr, at 100° C. The results are expressed in polystyrene equivalents.

The copolyester oligomers can be obtained by the usual molten-route, solvent-route or interface-route processes for preparing polyesters, these processes involving esterification reactions of diacids and of diols and polycondensation transesterification reactions of diesters and of diols and polycondensation autocondensation reactions of hydroxy acids Schotten-Baumann reactions using diols and acid chlorides, and polycondensation polymerization reactions of lactones while controlling the minimum content of units of formula (I) for which A represents a 1,4-phenylene group and n is equal to 1, which are similar on the basis of the initial stoichiometric ratios of the various monomers and on the basis of the control of the side reactions.

A particularly advantageous mode of preparation is that by molten-route transesterification/polycondensation and/or esterification/polycondensation using a transesterification and/or esterification catalyst.

The control of the structure is obtained by controlling the minimum content of units of formula (I) for which A represents a 1,4-phenylene group and n is equal to 1, which are similar on the basis of the initial stoichiometric ratios of the various diacid and/or diester and diol monomers and on the basis of the use of an etherification-limiting agent, it being possible for this limiting agent to be a basic compound such as aliphatic or aromatic amines, or an alkali-metal or alkaline-earth metal hydroxide or acetate.

The control of the molecular mass is obtained in a manner which is known per se to those skilled in the art, by achieving a suitable compromise between pressure, temperature and time.

The novel terephthalic copolyester oligomers which form the subject of the invention can be prepared by esterification and/or transesterification/polycondensation of a monomer composition based:

on terephthalic (Tp) acid, anhydride or diester
on sulphoisophthalic (SIp) acid, anhydride or diester
optionally on isophthalic (Ip) acid, anhydride or diester, and
on ethylene glycol (EG)

in relative amounts corresponding to
an (SIp)/[(Tp)+(SIp)+(Ip)] molar ratio preferably of at least 7/100, more preferably of at least 10/100, and most particularly of from 10/100 to 25/100
an (Ip)/[(Tp)+(SIp)+(Ip)] molar ratio preferably of not more than 20/100, more preferably of not more than 5/100
an (EG)/[(Tp)+(SIp)+(Ip)] molar ratio preferably of from 2/1 to 3/1
in the presence of an esterification and/or transesterification catalyst and an etherification-limiting agent.

The terephthalic (Tp) monomer is preferably used in the form of a lower diester (di($C_1$–$C_4$)alkyl diester), preferably the dimethyl diester.

The sulphoisophthalic (SIp) monomer is preferably used in the form of an alkali metal sulphonate (in particular sodium sulphonate) of a lower ($C_1$–$C_4$ alkyl), preferably methyl, diester. Sodium dimethyl 5-oxysulphonylisophthalate may be mentioned most particularly.

The optional isophthalic (Ip) monomer is preferably used in the form of isophthalic acid.

When all of the "diacid" monomers are used in the form of diesters, the transesterification (exchange) operation between these "diacid" monomers and ethylene glycol is carried out at a temperature preferably above or equal to 130° C., more preferably of about 140 to 220° C. and most particularly of about 180 to 220° C.; at this temperature the methanol (in the preferred case of the dimethyl diesters) formed is preferably removed from the reaction medium by distillation.

This exchange operation is carried out in the presence of a metallic transesterification catalyst and an etherification-limiting agent. The catalyst is preferably a metal carboxylate, such as manganese acetate, zinc acetate, cobalt acetate or calcium acetate, or an organic or inorganic titanate such as butyl titanate, nitrilo-2,2',2"-triethyl titanate (or titanium aminotriethanolate which also acts as etherification-limiting agent) or calcium titanate. The preferred catalysts are the organic titanates; they are preferably used in amounts of at least about 0.001% by weight, expressed as titanium, more preferably from about 0.002% to 0.02% by weight of titanium relative to the weight of reactants present.

The etherification-limiting agent can be a basic compound such as aliphatic or aromatic amines (triethanolamine, guanidine carbonate, dimethylaniline, naphthylamine, etc.) or an alkali-metal or alkaline-earth metal hydroxide or acetate (sodium or potassium acetate, sodium benzoate, etc.). It is generally used in an amount from about 0.001% to 0.05% relative to the weight of reactants present.

The duration of the exchange operation is preferably from 1 to 4 hours; more preferably from about 2 to 3 hours.

When more than 90% of the theoretical amount of methanol has been distilled off, the excess polyol is removed by bringing the temperature of the reaction medium to 230° C.

The polycondensation operation is preferably carried out at a temperature of about 230 to 280° C., more preferably of about 240 to 260° C., in another reactor brought beforehand to this temperature and gradually placed under vacuum down to a pressure which may be as low as 10 Pa; a pressure reduction down to about 10 millibar lasts for about 40 minutes.

The polycondensation operation takes place with removal of polyol molecules, this operation being stopped when the motor torque of the stirrer shaft indicates a value equivalent to about 0.5 to 5 newton.meters for a temperature of 250° C. of the reaction mass and a stirring speed of 80 revolutions/minute of an anchor-shaped spindle in a 7.5 liter reactor. The vacuum is then broken with nitrogen and the polymer is poured into a mould; after cooling, the polymer is ground.

When one of the "diacid" monomers is present in the form of diacid or anhydride and the other(s) is(are) in the form of diester(s), the said copolyester oligomers are obtained by first carrying out a transesterification operation of the diester monomers with ethylene glycol under the conditions described above, followed by an esterification operation in the medium of the diacid or anhydride monomer with ethylene glycol, and then polycondensation under the conditions described above, the total amount of ethylene glycol being divided between the two operations (transesterification and esterification).

If necessary, the esterification operation is carried out by adding, to the reaction medium resulting from the transesterification operation, monomer in diacid or anhydride form and ethylene glycol placed in suspension beforehand, at a temperature corresponding to that at the end of the exchange; the introduction period is about 1 hour.

This esterification operation is preferably carried out at a temperature of about 230 to 280° C., more preferably of about 250 to 260° C., in the presence of a catalyst of the same type as the transesterification catalyst, and an etherification-limiting agent.

The operation is carried out in the presence of the same types of catalyst and of etherification-limiting agent as those used in the transesterification operation, and in the same proportions.

The reaction is carried out with removal of water, which is removed from the reactor at the same time as the excess polyol.

This type of preparation process is described in particular in patent application WO 95/32997 (Rhône-Poulenc Chimie), the disclosure of which is specifically incorporated by reference herein.

Preferably, the composition according to the invention comprises from 0.001 to 40% by weight of terephthalic copolyester oligomer relative to the total weight of the composition. Depending on the desired liquid, pasty or solid form, various amounts of specific gelling agent will be used. For a solid composition, from 10 to 40% by weight of specific gelling agent will preferably be used, more preferably from 20 to 30% by weight. For a pasty composition, from 0.5 to 10% by weight of specific gelling agent will preferably be used, more preferably from 2 to 5% by weight. Smaller amounts will be used for a composition of liquid consistency.

The composition according to the invention is preferably a cosmetic or pharmaceutical composition intended to be applied to the skin, mucous membranes or the exoskeleton.

The composition can be used for any common dermocosmetic use, and in particular as a body hygiene composition, for example in the form of deodorant sticks ; as a hair composition for example as a styling gel; as a make-up composition, in particular as a so-called "transfer-free" make-up composition in particular a lip composition; as a care composition, for example a moisturizing lotion or alternatively as a oral or dental care composition like a toothgel or a toothpaste or a mouthwash.

The composition according to the invention can thus comprise other constituents that are common in cosmetics depending on the use which is envisaged.

The composition according to the invention can also comprise a fatty phase. The fatty phase can comprise oils or waxes that are common in cosmetics, of animal, plant, mineral or synthetic origin, alone or as mixtures.

The composition according to the invention can comprise additives and/or active agents that are common in dermocosmetics, it being understood that a person skilled in the art will know how to determine the amounts of these additives and active agents which may be added to the composition according to the invention so as not to adversely affect the properties of the specific gelling agent according to the invention.

The common cosmetic additives are, in particular, fragrances, dyes, odour absorbers, additives for stabilizing the composition, such as preserving agents, UVA and/or UVB screening agents, hydrophilic and/or lipophilic antioxidants, chelating agents, etc. The amounts of these various adjuvants are those used conventionally in the field considered, and, for example, from 0.0001 to 5% by weight relative to the total weight of the composition. Depending on their nature, these adjuvants can be introduced into the aqueous phase or into the fatty phase when the composition also comprises a fatty phase.

The composition according to the invention can also comprise hydrophilic and/or lipophilic active agents that are common in cosmetics, in particular anti-free-radical agents, α- or β-hydroxy acids, UVA and/or UVB screening agents, ceramides, antidandruff agents such as octopirox or zinc pyrithione, antiacne agents such as retinoic acid or benzoyl peroxide, agents for combating hair loss such as minoxidil, antifungal or antiseptic agents, oral or dental care agents, etc.

For use as a body hygiene composition, the composition according to the invention can comprise deodorant products containing active substances of antiperspirant type and/or of bactericidal type in order to reduce or even eliminate the generally unpleasant underarm odours, and/or odour absorbers.

For use as a hair composition, owing to the specific rheological properties of the gel constituting it, the composition according to the invention affords a good styling effect and discipline to the hair style.

In order to obtain a fixing effect or to improve the styling and disentangling effect, a fixing material or a conditioning material can be added to the composition according to the invention. These fixing or conditioning materials can be used in amounts preferably ranging from 0.01 to 15% by weight relative to the total weight of the composition, more preferably from 0.1 to 8% by weight.

The composition according to the invention can also comprise haircare active agents and/or sheen-reinforcing agents and/or hair dyes. These active agents and/or hair agents can be used in amounts preferably ranging from 0.01 to 20% by weight relative to the total weight of the composition according to the invention.

For use as a make-up composition, the composition according to the invention can comprise materials that are common for make-up compositions, in particular fillers and/or dyestuffs.

When the composition is a care composition, it comprises active agents such as ascorbic acid, kojic acid, citric acid, caffeic acid, salicylic acid and its derivatives (for example 5-n-octanoylsalicylic or 5-decanoylsalicylic acid), a-hydroxy acids, retinoic acid and its derivatives such as retinol and retinol esters, benzene-1,4-di(3-methylidene-10-camphorsulphonic acid). Any natural or synthetic compound containing such acids, such as plant extracts and more especially fruit extracts, can also be used. Xanthine derivatives (caffeine, theophylline), β-glycyrrhetinic acid or asiatic acid can also be dissolved therein.

Depending on the use envisaged and on the physico-chemical and/or cosmetic properties of the composition according to the invention, it can also comprise additional gelling agents so as to modify its properties of softness or of hardness, and it can additionally comprise lattices or pseudolattices which increase the remanence to water of the composition and give it sheen, or alternatively one or more silicone gums which give the final compositions qualities of softness and slipperiness.

A person skilled in the art will know how to determine the process for preparing the composition according to the invention as a function of its constituents.

The present invention also relates to a cosmetic treatment process for the skin, mucous membranes, the hair or the exoskeleton, in which the composition as defined above is applied to the skin, mucous membranes or the exoskeleton.

The examples below allow the present invention to be illustrated without, however, seeking to limit its scope. The percentages are expressed on a weight basis relative to the total weight of the composition. The percentages of ethylene glycol isophthalate/terephthalate/sulphoisophthalate copolymer in the compositions are percentages of active material. For Examples 3 and 4, the viscosities were measured at 25° C. with a control stress rheometer (HAAKERS 150) having a cone-plate measurement device with a one (1) degree angle and a diameter (Φ) of 3.5 cm.

EXAMPLE 1

Preparation of a terephthalic copolyester oligomer according to the invention

The following reactants were introduced into a 7.5 liter stainless-steel reactor fitted with an anchor-shaped stirrer rotating at 80 rev/min, connected to a Kyowa torsion meter, a jacket for circulating a heat-exchange liquid, and a distillation column controlled by an electrovalve:

11.47 mol of dimethyl terephthalate 2.53 mol of sodium dimethyl isophthalate-5 sulphonate 39.16 mol of ethylene glycol 54 ppm by weight of titanium, in the form of titanium aminotriethanolate as catalyst and etherification-limiting agent.

The mixture was preheated to 180 ° C. It was then brought to a temperature of 220° C. over about 130 minutes, in order to distil off more than 90% of the theoretical amount of methanol.

The reaction mixture was then brought to 230° C. over 30 minutes. When the reaction mass reached this temperature, a suspension having the composition below was introduced over 60 minutes, still at 230° C.:

0.5 mol of isophthalic acid 2.36 mol of terephthalic acid 8 mol of ethylene glycol The reaction mass was then brought to a temperature of 250° C. over 60 minutes.

During the period of introduction of the mixture and during the period of heating up to 250° C., a mixture of water and ethylene glycol were distilled off without retrogradation.

The reaction mixture was then transferred into an autoclave preheated to 250° C. and was then placed under a reduced pressure of 100 millibar over 22 minutes. After 2 minutes under these temperature and pressure conditions, the reaction mass was cast and cooled.

The copolyester obtained had the structural characteristics described in Table 1.

EXAMPLE 2

Preparation of a terephthalic copolyester oligomer not according to the invention The following reactants were introduced into a stainless-steel reactor identical to that described in Example 1:

15.16 mol of dimethyl terephthalate 1.99 mol of sodium dimethyl isophthalate-5 sulphonate 48 mol of ethylene glycol 54 ppm by weight of titanium, in the form of butyl orthotitanate as catalyst and etherification-limiting agent.

The mixture was preheated to 180° C. It was then brought to a temperature of 220° C. over about 130 minutes, in order to distil off more than 90% of the theoretical amount of methanol.

The reaction mixture was then brought to 250° C. over 90 minutes. When the reaction mass reached this temperature, the reaction mixture was transferred into an autoclave preheated to 250° C. and was then placed under a reduced pressure of 1 millibar over 60 minutes. The reaction mixture was then maintained under these temperature and pressure conditions for 90 minutes, after which the reaction mass was cast and cooled.

The copolyester obtained had the structural characteristics described in Table 1.

In this table:

"mol % of diacid units" corresponds to the content, in %, of each diacid or diester used relative to the total amount of diacids or diesters used.

"Tp" means: terephthalic unit

"Ip" means: isophthalic unit

"SIp" means: sulphoisophthalic unit

The characteristics of the "glycol" part of the copolyesters were obtained by methanolysis of the products at 190° C. for 16 hours, followed by analysis by the gas chromatography technique and assaying by internal calibration.

"mol % of diol units" corresponds to the content, in %, of oxyethylene units "G", di(oxyethylene) units "2G", tri(oxyethylene) units "3G" and tetra(oxyethylene) units "4G", relative to the total amount of diol units.

"% GT/Σ units" corresponds to the mol % of units of formula (I)

$$[-CO-A-CO-O-(CH_2-CH_2-O)_n-] \quad (I)$$

where A is 1,4-phenylene and n=1 relative to the total amount of units of formula (I) wherein A is 1,4-phenylene, sulpho-1,3-phenylene or 1,3-phenylene and n ranges from 1 to 4

"% GT/Σ units" is calculated by the following formula:

% GT/Σ units=(mol % of Tp units)×(mol % of G units)/100

The molar mass of the polyesters (Mw) was determined by gel permeation chromatography (GPC) in 100% DMAc/LiBr, the results being given in polystyrene equivalents.

| Example | 1 | 2(comparative) |
|---|---|---|
| mol % of the diacid units | | |
| Tp | 82 | 88.4 |
| Ip | 3 | 0 |
| SIp | 15 | 11.6 |
| % GT/Σ units | 46.5 | 47 |
| mol % of the diol units | | |
| G | 56.8 | 52.8 |
| 2G | 30.7 | 34.2 |
| 3G | 10 | 10.7 |
| 4G | 2.5 | 2.3 |
| Mw | 8000 | 50,000 |

EXAMPLE 3

Gel containing 20% oligomer

An aqueous gel was prepared by mixing, under cold conditions, 20% of oligomer of Example 1 and the remainder to 100% of demineralized water. The fluid gel obtained is poured into a mould and left to stand for 24 hours. After setting to a solid, a styling stick with an initial viscosity equal to 90,000 Pa.s is obtained. Under a shear strain of 1500 Pa, the viscosity is 30 Pa.s.

Such rheological characteristics allow the application of films using the solid topical composition according to the invention, on soft or moving surfaces such as the hair.

In contrast, with the polymer of Example 2 (comparative), which differs from the oligomers according to the invention by a weight-average molecular mass of 50,000, the 20% by weight aqueous composition remains liquid even after leaving to stand for more than 24 hours.

EXAMPLE 4

Gel containing 8% oligomer

An aqueous gel was prepared by mixing, under cold conditions, 8% of oligomer of Example 1 and the remainder to 100% of demineralized water. The fluid gel obtained was poured into a mould and left to stand for 24 hours. After setting to a solid, measurement of the gel obtained shows an initial viscosity of 30,000 Pa.s and a viscosity under a shear strain at 105 Pa of 30 Pa.s.

EXAMPLE 5

Conditioning gel

The procedure of Example 3 can be repeated with the following constituents:

Oligomer of Example 1 5% am polyaminosiloxane (sold under the name DC 939 by the company Dow Corning) 2% am Water qs 100%

We claim:

1. A topical composition comprising an aqueous phase containing a hydrophilic polyester sulphone gelling agent selected from water-soluble and water-dispersible terephthalic copolyester oligomers comprising repeating dicarboxylate units of formula (I):

$$-CO-A-CO-O-(CH_2CH_2O)_n- \quad (I)$$

in which
- A represents a 1,4-phenylene, sulpho-1,3-phenylene or 1,3-phenylene group,
- n ranges from 1 to 4, wherein
- in at least 35 mol % of said units of formula (I), A represents a 1,4-phenylene group and n is equal to 1,
- in at least 7 mol % of said units of formula (I), A represents a sulpho-1,3-phenylene group, and
- optionally, in up to 20 mol % of said units of formula (I), A represents a 1,3-phenylene group, and further wherein the weight-average molecular weight of said copolyester oligomer is less than 20,000.

2. A topical composition according to claim 1, wherein said weight-average molecular weight is less than 15,000.

3. A topical composition according to claim 1, wherein A represents a 1,4-phenylene group in at least 40 mol % of said units of formula (I).

4. A topical composition according to claim 3, wherein A represents a 1,4-phenylene group in from 40 to 90 mol % of said units of formula (I).

5. A topical composition according to claim 1, wherein A represents a sulpho-1,3-phenylene group in at least 10 mol % of said units of formula (I).

6. A topical composition according to claim 5, wherein A represents a sulpho-1,3-phenylene group in from 10 mol % to 25 mol % of said units of formula (I).

7. A topical composition according to claim 1, wherein A represents a 1,3-phenylene group in up to 5 mol % of said units of formula (I).

8. A topical composition according to claim 2, wherein said copolyester oligomer has a weight-average molecular weight ranging from 5000 to 14,000.

9. A topical composition according to claim 8, wherein said copolyester oligomer has a weight-average molecular weight ranging from 8000 to 10,000.

10. A topical composition according to claim 1, wherein said terephthalic copolyester oligomer is present in an amount ranging from 0.001 to 40% by weight relative to the total weight of said topical composition.

11. A topical composition according to claim 10, wherein said terephthalic copolyester oligomer is present in an amount ranging from 10 and 40% by weight relative to the total weight of said topical composition.

12. A topical composition according to claim 11, wherein said terephthalic copolyester oligomer is present in an amount ranging from 20 and 30% by weight relative to the total weight of said topical composition.

13. A topical composition according to claim 10, wherein said terephthalic copolyester oligomer is present in an amount ranging from 0.5 to 10% by weight relative to the total weight of said topical composition.

14. A topical composition according to claim 13, wherein said terephthalic copolyester oligomer is present in an amount ranging from 2 to 5% by weight relative to the total weight of said topical composition.

15. A topical composition according to claim 1, wherein said topical composition is a cosmetic or pharmaceutical composition.

16. A topical composition according to claim 15, wherein said topical composition is a body hygiene composition, a hair composition, a make-up composition or a care composition.

17. A topical composition according to claim 1, wherein said topical composition further comprises at least one additive and/or active agent common in dermocosmetics.

18. A topical composition according to claim 17, wherein said at least one additive and/or active agent are chosen from: fragrances; stabilizing agents; UV-A and UV-B screening agents; hydrophilic and lipophilic antioxidants; chelating agents; α- and β-hydroxy acids; ceramides; antidandruff agents; antiacne agents; agents for combating hair loss; antifungal and antiseptic agents; antiperspirant active substances, bactericidal active substances, and odor absorbing active substances; hair fixing material and conditioning material; hair care active agents and sheen-reinforcing agents and hair dyes; fillers, dyes and dyestuffs; gelling material; and silicone gums.

19. A topical composition according to claim 1, wherein said topical composition further comprises at least one lattice or pseudolattice.

20. A topical composition according to claim 16, wherein said make-up composition is a transfer-free make-up composition.

21. A topical composition according to claim 16, wherein said topical composition is a lip composition or an oral or dental care composition.

22. A topical composition according to claim 21, wherein said oral or dental care composition is selected from a toothgel, a toothpaste and a mouthwash.

23. A process of cosmetically treating human skin, a mucous membrane or exoskeleton comprising applying an effective amount of a topical composition according to claim 1 to said skin, mucous membrane or exoskeleton.

* * * * *